United States Patent [19]

Levinson et al.

[11] Patent Number: 5,727,547
[45] Date of Patent: Mar. 17, 1998

[54] PRESENTING PART FETAL OXIMETER SENSOR WITH SECURING MECHANISM FOR PROVIDING TENSION TO SCALP ATTACHMENT

[75] Inventors: Mitchell Levinson, Pleasanton; Steven L. Nierlich, San Leandro; Paul Mannheimer, Danville, all of Calif.

[73] Assignee: Nellcor Puritan Bennett Incorporated, Pleasanton, Calif.

[21] Appl. No.: 706,482

[22] Filed: Sep. 4, 1996

[51] Int. Cl.$^6$ ............................................. A61B 5/00
[52] U.S. Cl. ............................................. 128/633
[58] Field of Search ................................. 128/633, 634, 128/642, 664–7, 698, 897, 898

[56] References Cited

U.S. PATENT DOCUMENTS

| | | | |
|---|---|---|---|
| 4,658,825 | 4/1987 | Hochberg et al. | 128/634 |
| 5,154,175 | 10/1992 | Gunther | 128/633 |
| 5,291,896 | 3/1994 | Fonger et al. | 128/713 |
| 5,357,955 | 10/1994 | Wolf et al. | 128/634 |
| 5,411,024 | 5/1995 | Thomas et al. | 128/634 |
| 5,569,186 | 10/1996 | Lord et al. | 128/635 |

Primary Examiner—Jennifer Bahr
Assistant Examiner—Bryan K. Yarnell
Attorney, Agent, or Firm—Townsend and Townsend and Crew LLP

[57] ABSTRACT

A presenting part fetal pulse oximeter sensor with a securing mechanism for providing tension to a hook or other securing mechanism penetrating the fetal scalp. In one embodiment, a sensor can be secured to the presenting part of the fetus by means of a suture or a hook which penetrates the fetus' scalp. If a suture is used, the ends of the suture are wrapped around a securing member, such as a bar, attached to the back of the sensor. By tying the suture ends around this securing member, the sensor is pressed up against the fetus' scalp and retained in place by virtue of tension provided in the suture between the securing member and the portion of the suture penetrating the fetus' scalp.

7 Claims, 2 Drawing Sheets

PRESENTING PART FETAL OXIMETER SENSOR WITH SECURING MECHANISM FOR PROVIDING TENSION TO SCALP ATTACHMENT

BACKGROUND OF THE INVENTION

The present invention relates to a non-invasive pulse oximetry fetal intrauterine sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Known non-invasive sensors include devices that are secured to a portion of the body, such as a finger, ear or the scalp. In animals and humans, the tissue of these body portions is perfused with blood and the tissue surface is readily accessible to the clinician.

It is desirable that photoelectric pulse oximetry also be useful for monitoring the blood flow characteristics and constituents of a fetus. For example, monitoring fetal oxygen levels provides an effective way to detect and provide indications for treating hypoxia in the fetus during labor. However, known sensors adapted for use on infants or adults are not suited for intrauterine placement.

The environment in which the non-invasive intrauterine sensor must operate is fluid-filled (e.g., by amniotic fluid) and is only accessible through the restricted opening of the cervix. Visual inspection of the fetus and the sensor is likewise restricted. Moreover, the operating environment presents certain variants that interfere with detection of the fetal blood flow characteristics using known pulse oximetry techniques. For example, the presence of the waxy vernix caseosa, hair, mucus, blood and dead tissue cells on top of the fetal tissue surface against which the sensor is to be positioned create a problem in establishing contact between the optical components of the sensor and the surface of blood-perfused tissue. Detection of fetal blood flow characteristics by pulse oximetry is particularly complicated by the relatively low perfusion and low oxygen saturation of blood in fetal tissue. These environmental factors prevent known sensors from providing reliable information needed to calculate fetal blood characteristics.

It is known that positive attachment of a sensor to the tissue surface improves the quality of the photoelectric signal provided by the sensor. Positive attachment to a human's tissue may be obtained by vacuum, adhesives, tapes or devices such as clothespin-type clips. However, fetal tissue is relatively moist and there is limited access to the tissue surface. Consequently, conventional adhesives or tapes or clips are not adapted for intrauterine use.

There are two basic types of fetal sensors, presenting part sensors and beyond the presenting part sensors. "Presenting part" refers to the region of the fetus that, during labor, resides external to the cervical os. "Beyond the presenting part" falls within the uterus and extends out to the cervical os. Sensors beyond the presenting part can typically use the uterine wall to bias the sensor against the fetus. For the presenting part, however, the fetus' scalp is typically exposed to the open birth canal, and such biasing is not as readily available, with positive attachment usually being used.

Presenting Part Sensors

Known techniques for presenting part sensors include invasive attachment to fetal tissue, such as by a screw attachment penetrating the tissue, or vacuum attachment mechanisms.

Examples of presenting part sensors include U.S. Pat. No. 3,827,428 which discloses a heartbeat sensor using a coil screw for attaching to the fetus' scalp. Pulse oximeter and other sensors which use such a spiral or screw-type arrangement are also shown in U.S. Pat. Nos. 4,281,659; 4,658,825; 5,154,175; 5,361,757; 5,411,024; and German Published Application No. DE4304691A1.

Examples of vacuum-type fetal sensors include that shown in U.S. Pat. No. 4,938,218 and PCT Published Application No. W091/15996, which shows a bellows for providing a low-pressure vacuum source. U.S. Pat. No. 4,537,197 shows another vacuum attachment fetal sensor.

A number of other designs are also known. U.S. Pat. No. 4,299,232 shows a combination of a suction adhesion with a suction-cup type attachment, in conjunction with an electrical pole which pierces the fetus' skin. U.S. Pat. No. 5,024,226 requires a bore hole in the brain of the patient. U.S. Pat. No. 4,543,965 uses an inflatable membrane to bias the sensor against the fetus at the presenting part.

Non-Presenting Part Sensors

Other fetal sensors are designed to go beyond the presenting part. For instance, U.S. Pat. No. 5,247,932 shows a bladder between the fetus and the uterine wall which presses the active face of the sensor against the fetus' skin. U.S. Pat. No. 5,377,675 discloses a sensor using a fulcrum to bias the sensor against the fetus. PCT Published Application No. W091/07910 uses an inflatable sac to wedge the sensor against the fetus.

The intrauterine probe sensor must be safely and reliably deliverable to the point of contact with the fetus. It is desirable that intrauterine fetal monitoring be available early in labor, for example, to detect and treat hypoxia in the fetus during labor. Contact with the fetus can be made after natural rupture of the amniotic membrane by manually inserting a probe sensor into the uterus from the vagina, but access to the fetus through the vaginal canal is restricted by the cervix, which may be only slightly dilated to one or two centimeters when the membrane ruptures. Thus there is need for a fetal probe sensor that can be delivered to the fetus through a slightly dilated cervix, and a delivery system for doing so safely and reliably.

A presenting part sensor is often desirable for a variety of reasons. First, it is less invasive than a beyond the presenting part sensor. Second, a presenting part sensor may be used for spot-checking saturation rather than continuous monitoring. Third, a presenting part sensor may be necessary for monitoring fetus' located high in the uterus. Fourth, a presenting part sensor is easy to place and may be more reliably attached than a beyond-the-presenting part sensor.

SUMMARY OF THE INVENTION

The present invention provides a presenting part fetal pulse oximeter sensor with a securing mechanism for providing tension to a hook or other securing mechanism penetrating the fetal scalp.

In one embodiment, a sensor can be secured to the presenting part of the fetus by means of a suture or a hook which penetrates the fetus' scalp. If a suture is used, the ends of the suture are wrapped around a securing member, such as a bar, attached to the back of the sensor. By tying the suture ends around this securing member, the sensor is pressed up against the fetus' scalp and retained in place by virtue of tension provided in the suture between the securing member and the portion of the suture penetrating the fetus' scalp.

In an alternative embodiment, rather than a suture, a hook may be placed in the fetus' scalp. The hook may have a suture-type thread or other flexible attachment to the end of the hook which can be attached to a securing member on, for instance, a backside of a sensor to draw the sensor up against the fetus' scalp.

The present invention thus provides a simple method of attaching a sensor to a fetus which will hold the sensor securely, without requiring any continuous, external tension to ensure that the sensor stays in place.

For a fuller understanding of the nature and advantages of the invention, reference will be made to the following description taken in conjunction with the accompanying drawings.

DESCRIPTION OF THE PREFERRED EMBODIMENT

Figure 1:
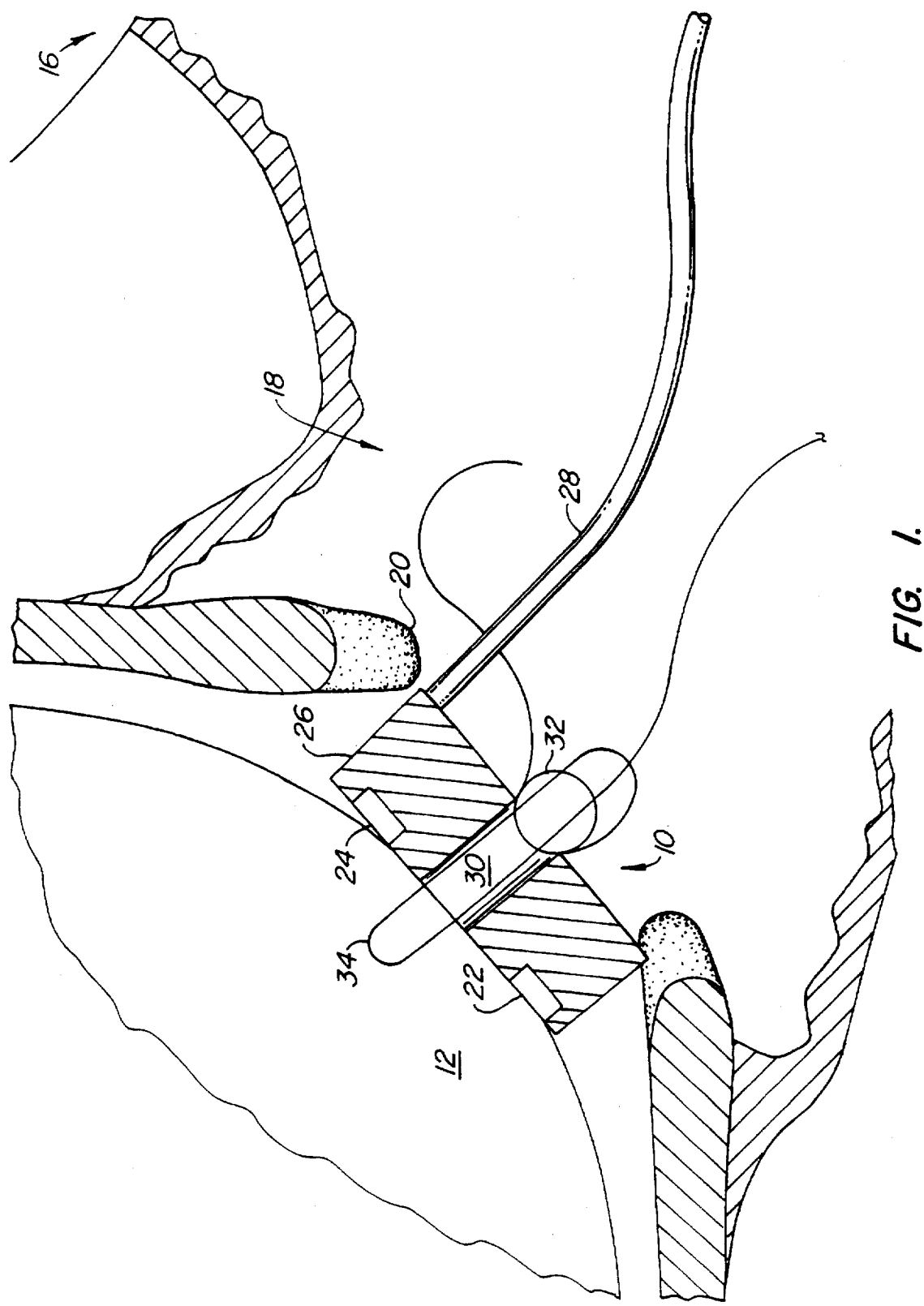
FIG. 1 is a drawing illustrating a securing member according to the present invention and used with a suture.

FIG. 1 illustrates the application of a first embodiment of a sensor 10 according to the present invention to a fetus' scalp 12. The sensor is inserted through the vagina 16 and birth canal 18 and past the cervix 20 to the fetus' scalp 12.

The sensor includes a light emitter 22 and a light detector 24. The light emitter and detector are mounted in a sensor body 26, which is attached to a cable 28 for providing signals to and from the emitter and detector.

The sensor includes a central open area 30, with a retaining member 32 at the back end, away from the fetus' head. Member 32 can be a rod, for example, connecting across the width, or alternatively the length, of sensor body 26.

A suture 34 is passed through the fetus' scalp using a suture needle in the hands of a physician or technician. Alternately, a tool may be used to attach the suture to the fetus' scalp prior to application of the sensor, or after application of the sensor through the gap 30.

The suture is then wound around retaining member 32 and tied off to bias the sensor against the fetus' scalp by the tension between the portion of the suture penetrating the fetus' scalp and the portion of the suture wound around retaining member 32.

As can be seen, the present invention provides a method for applying tension to hold the sensor against the fetus' scalp, with the use of a thread or other flexible material which can be attached to a securing mechanism, thereby eliminating the need for complicated mechanical advancing mechanisms for securing to a fetus' head as in the prior art.

Figure 2:
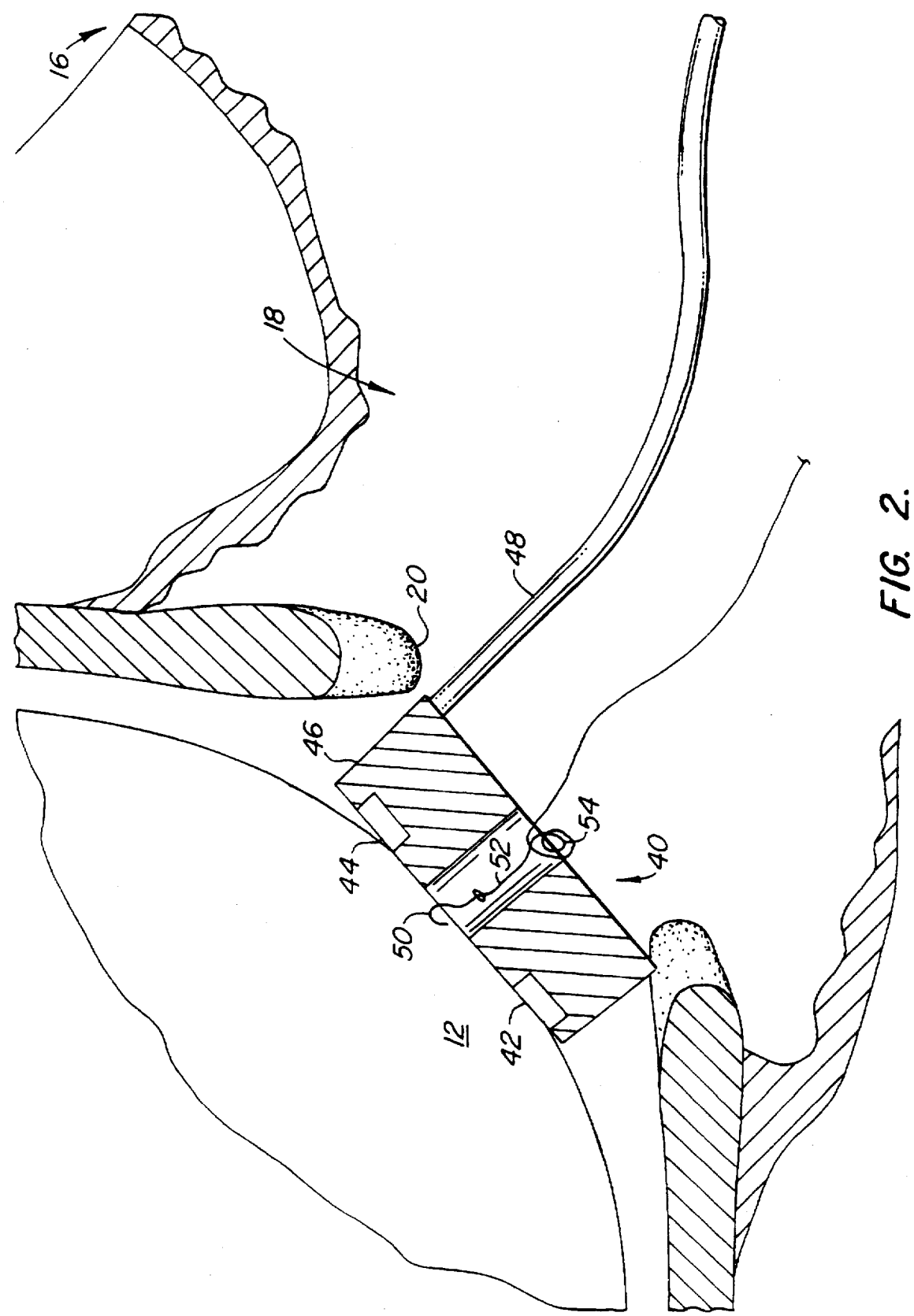
FIG. 2 is a diagram of a second embodiment of the present invention in use with a hook.

FIG. 2 illustrates an alternative embodiment of the present invention. Again, a sensor 40 is passed through a vagina 16, a birth canal 18, and passed a cervix 20 to be placed up against a fetus' scalp 12. The sensor includes a light emitter 42 and a light detector 44. The light emitter and detector are mounted in a sensor body 46, and a cord 48 provides electrical or fiber optic connections to the emitter and detector.

In the embodiment of FIG. 2, a hook 50 is embedded into the fetus' scalp, with a thread or other flexible material 52 being attached to the back end of the hook. Thread 52 is then wound around a member 54 to apply tension to hook 50, and is either tied off at member 54, or can be secured remotely to the mother's birth canal.

Alternatively, thread or flexible member 52 could be a bungee-type material with a second hook for hooking around member 54. Thus, tension could be applied by the resiliency of the securing member, which also allows it to be stretched to place the second hook around member 54. This eliminates the need for tying off the thread.

Note that alternative embodiments of the sensor are possible, such as having the emitter and detector on the same side of the hook, or reversed from the position shown in FIG. 2.

As will be understood by those of skill in the art, the present invention may be embodied in other specific forms without departing from the spirit or essential characteristics thereof. Accordingly, the foregoing description is intended to be illustrative of the preferred embodiment of the invention, but not limiting of the scope of the invention, which is set forth in the following claims.

What is claimed is:

1. A perinatal pulse oximeter sensor for application to a presenting part of a fetus and measurement of blood oxygen saturation, comprising:

a sensor head having a fetus engaging surface for engagement with the presenting part of said fetus;

light emitting means connected to said sensor head for emitting light of at least two wavelengths directed at said presenting part of said fetus;

light detecting means mounted in said sensor head for collecting light to be detected;

attachment means for passing through a tissue of the presenting part of said fetus; and a securing and tensioning member, connected to said sensor head a distance away from said engaging surface, for securing and applying tension to said attachment means after it is passed through said tissue of said fetus.

2. The perinatal pulse oximeter sensor of claim 1 wherein: said attachment means includes a hook for passing through the tissue of said fetus.

3. The perinatal sensor of claim 1 wherein said attachment means comprises a suture.

4. The perinatal sensor of claim 1 wherein said securing member comprises a bar extending across an opening on a backside of said sensor.

5. The perinatal sensor of claim 1 wherein said attachment means is resilient, and further comprising a hook connected to said attachment means.

6. The perinatal sensor of claim 1 wherein said attachment means is detachable from said sensor.

7. A perinatal pulse oximeter sensor for application to a presenting part of a fetus and measurement of blood oxygen saturation, comprising:

a sensor head having a fetus engaging surface for engagement with the presenting part of said fetus;

light emitting means connected to said sensor head for emitting light of at least two wavelengths directed at said presenting part of said fetus;

light detecting means mounted in said sensor head for collecting light to be detected;

a suture for passing through a tissue of the presenting part of said fetus, said suture being detachable from said sensor; and a securing and tensioning bar, connected across an opening in said sensor head, for securing and applying tension to said suture after it is passed through said tissue of said fetus.

* * * * *